United States Patent [19]

Halmos

[11] 4,210,593

[45] Jul. 1, 1980

[54] PROCESS FOR PREPARING ACETYLSULFAGUANIDINE

[75] Inventor: Imre A. Halmos, Summit, N.J.

[73] Assignee: American Cyanamid Company, Stamford, Conn.

[21] Appl. No.: 902,597

[22] Filed: May 4, 1978

[51] Int. Cl.$^2$ .......................................... C07C 143/58
[52] U.S. Cl. ..................................... 397.7 R; 424/321
[58] Field of Search ................................. 260/397.7 A

[56] References Cited

U.S. PATENT DOCUMENTS

| | | | |
|---|---|---|---|
| 2,380,006 | 7/1945 | Winnek et al. | 260/397.7 |
| 2,463,793 | 3/1949 | Mosnier | 260/397.7 |

FOREIGN PATENT DOCUMENTS 1065407  9/1959  Fed. Rep. of Germany ........ 260/397.7

OTHER PUBLICATIONS

Copson, Microwave Heating, pp. 371 to 372, The Avi Publishing Co., Inc., Conn. USA (1962).
Chem. Abstracts, vol. 55, col. 8355b (1961).

Primary Examiner—John D. Randolph
Attorney, Agent, or Firm—Charles F. Costello, Jr.

[57] ABSTRACT

A method suitable for the continuous preparation of acetylsulfaguanidine is described which comprises exposing a thin layer of a concentrated aqueous solution of ammonium acetylsulfanilylcyanamide to microwave radiation until essentially anhydrous ammonium acetylsulfanilylcyanamide is obtained in the form of a glassy, non-crystalline sheet, and converting the dry ammonium acetylsulfanilylcyanamide to acetylsulfaguanidine by heating.

4 Claims, No Drawings

PROCESS FOR PREPARING ACETYLSULFAGUANIDINE

BACKGROUND OF THE INVENTION

This invention relates to an improved process for the preparation of acetylsulfaguanidine. More particularly this invention relates to a continuous process for the preparation of acetylsulfaguanidine from ammonium acetylsulfanilylcyanamide.

The transformation of ammonium acetylsulfanilylcyanamide (AASC) to acetylsulfaguanidine (ASG) is illustrated by the following reaction:

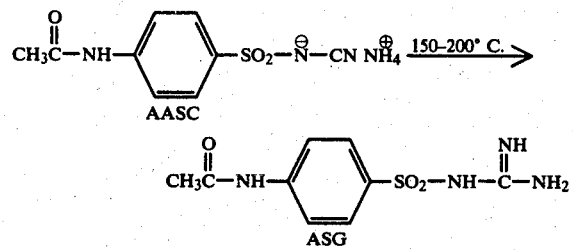

ASG is a well-known compound which is convertible into sulfaguanidine, an important chemotherapeutic agent, useful in the treatment of various intestinal infections. Sulfaguanidine is particularly valuable for such use since it is not readily absorbed from the gastrointestinal tract, thus minimizing toxicity. It is also useful as an intermediate for the synthesis of other chemotherapeutic agents.

Mosnier in Example 2 of U.S. Pat. No. 2,463,793 discloses a process wherein a 50% aqueous solution of AASC is transformed to ASG by autoclaving at 150°–155° C. for 2 hours, cooling the reaction mixture and collecting the insoluble ASG by filtration. However, the yields obtained in this process are low.

In Example 1 of Mosnier a process is disclosed wherein AASC is crystallized from aqueous solution and the crystalline salt is converted to ASG by heating at 150°–170° C. The resulting melt congeals to a solid mass. However, in this process the yield of crystalline AASC obtained is low because of high solubility in water and the crystals obtained contain water of hydration which cannot be readily removed by drying. Also, the crystals obtained cannot be uniformly heated without splashing or bubbling occurring. Furthermore, the AASC congeals into a solid mass of ASG which is difficult to handle.

There is a need for an improved process wherein concentrated aqueous solutions of AASC can be converted to ASG in higher yields and which avoids the processing of congealed ASG.

SUMMARY OF THE INVENTION

The discovery has now been made that a concentrated aqueous solution of ammonium acetylsulfanilylcyanamide can be transformed to acetylsulfaguanidine by a process wherein a layer of AASC solution is continuously and rapidly dried by microwave irradiation to form a glassy sheet of essentially anhydrous ammonium acetylsulfanilylcyanamide, the internal temperature of which ranges from about 70° C. to about 130° C., and wherein said glassy sheet is transformed to acetylsulfaguanidine by further microwave irradiation, or heating, at 150°–200° C. to form a glassy layer of acetylsulfaguanidine which on fracturing assumes a crystalline state and is recovered.

The process of this invention offers the following advantages:

1. The acetylsulfaguanidine is obtained in essentially quantitative yield.
2. The product has a higher degree of purity than acetylsulfaguanidine obtained by the transformation of crystalline hydrated ammonium acetylsulfanilylcyanamide.
3. The product is obtained in a form which is easily handled.
4. The energy required to produce the essentially anhydrous ammonium acetylsulfanilylcyanamide is very low.

The process for preparing acetylsulfaguanidine comprises:

adding a concentrated aqueous solution of ammonium acetylsulfanilylcyanamide as a thin layer to a container;

subjecting the layer to microwave radiation for between about 30–90 seconds to form a soft glassy sheet of essentially anhydrous ammonium acetylsulfanilylcyanamide having a temperature between about 70°–130° C.;

removing the sheet from the microwave radiation;

heating the sheet at about 150°–200° C. to form a soft glassy sheet of acetylsulfaguanidine with the proviso that the heating means does not generate an electromagnetic wavelength between about 1 and 100 centimeters;

cooling the sheet of acetylsulfaguanidine to ambient temperature to form a hard glassy sheet of acetylsulfaguanidine; and recovering essentially pure acetylsulfaguanidine from the container. In the preferred process the aqueous solution contains 50–60% by weight of ammonium acetylsulfanilylcyanamide, the layer is subjected to microwave radiation for about 60–80 seconds to form the sheet of anhydrous ammonium acetylsulfanilylcyanamide having a temperature between about 70°–105° C., and the sheet is further heated at about 180°–200° C. between about 10–15 minutes to form the soft glassy sheet of acetylsulfaguanidine. In another preferred process the heating means is an infrared radiation.

Alternatively, the process for preparing acetylsulfaguanidine comprises:

adding a concentrated aqueous solution of ammonium acetylsulfanilylcyanamide as a thin layer to a container;

subjecting the solution to microwave radiation for between about 30–90 seconds to form a soft glassy sheet of essentially anhydrous ammonium acetylsulfanilylcyanamide having a temperature between about 70°–130° C.;

removing the sheet from the microwave radiation;

resubjecting the sheet to microwave radiation whereby the temperature of the sheet is raised to about 150°–200° C. and forms a soft glassy sheet of acetylsulfaguanidine;

cooling the sheet of acetylsulfaguanidine to ambient temperature to form a hard glassy sheet of acetylsulfaguanidine; and recovering essentially pure acetylsulfaguanidine from said container. In the preferred alternative process the aqueous solution contains 50–60% by weight of ammonium acetylsulfanilylcyanamide, the layer is subjected to microwave radiation for about 60–80 seconds to form the sheet of anhydrous ammonium acetylsulfanilylcyanamide having a temperature of about 70°–105° C., and the sheet is resubjected to microwave radiation at about 160°–180° C. for between about 1–2 minutes to form a glassy sheet of acetylsulfaguanidine.

DESCRIPTION OF PREFERRED EMBODIMENT

Ammonium acetylsulfanilylcyanamide (AASC) can be prepared as a concentrated aqueous solution by reacting equimolar amounts of the calcium salt of acetylsulfamilylcyanamide and ammonium carbonate in water, removing the calcium carbonate precipitate, and recovering the filtrate which contains 50–70% AASC. The preparation of the calcium salt of acetylsulfanilylcyanamide is disclosed by Winnek et al, Jour. Am. Chem. Soc. 64, (1942), pp. 1682–1685, the disclosure of which is incorporated herein by reference.

The concentrated solution of AASC is continuously applied as a layer to a suitable conveyor device and subjected to microwave radiation to evaporate the water and form an essentially anhydrous glassy sheet of AASC. Preferably, the glassy sheet is about 1–3 mm. in thickness.

As used herein the term "suitable conveyor device" is defined as a movable device for receiving a layer of aqueous solution up to 20 mm. in thickness, said device being made of a material which does not absorb microwave radiation, such as Teflon ®, DuPont Co., Wilmington, Del. or a material which does not rapidly dissipate heat through thermal conduction, such as fiber glass.

In the process of this invention concentrated aqueous solutions of 50–70% by weight AASC, preferably 50–60%, are continuously added as a layer to said suitable conveyor device. More preferably, a biodegradable organic phosphate ester, Emcol ® PS 220 (Witco Chemical Corp.), is included at about 2% by weight in the aforementioned concentrated aqueous solutions as a dispersant.

Solutions containing 50–70% by weight AASC can be quickly dried to an essentially anhydrous glassy state by continuously applying a layer of said solution to the conveyor device at an entry port of a microwave oven and passing the device through the oven under microwave radiation.

Microwave radiation, as used herein, is defined as electromagnetic radiation having a frequency from 300 to 300,000 mega Hertz (MHz.). The frequencies 915 and 2450 MHz. are used industrially. when microwave radiation impinges upon a substance containing polar molecules, such as water, the energy is absorbed by the polar molecules thus generating heat. The value of microwave drying lies in the fact that water can be selectively and uniformily evaporated. This property is particularly valuable in drying AASC because in conventional drying operations AASC must be heated at about 100° C. to vaporize the water from the hydrated salt. Using microwave radiation it is possible to obtain essentially anhydrous AASC having about 70°–130° C. internal layer temperature, preferably about 70°–105° C., in a very short time. The internal temperature obtained will depend on the intensity and duration of irradiation.

The thin layer of aqueous solution applied to the conveyor device can be less than 2 mm. thick. Thicker layers may be applied depending on the material of construction of the device. In the process of this invention the aqueous layer is subjected to microwave irradiation to evaporate the water and form an essentially anhydrous glassy sheet of AASC in about 30–90 seconds, preferably 60–80 seconds, depending on the material of construction of the device.

The essentially anhydrous glassy sheet of AASC may be further irradiated in the microwave oven to convert it to ASG, or converted to ASG by heating in a tubular heating device.

The term "tubular heating device," as used herein, is defined as a longitudinal cavity having an entry port for receiving said conveyor device having the glassy sheet of AASC deposited thereon and an exit port for the exit of said conveyor device to a cooling zone. The longitudinal cavity has a source of heat whereby the temperature of the glassy sheet is raised to about 150°–200° C., preferably about 180°–200° C., and maintained at said temperature for a residence period sufficiently long enough to transform the glassy sheet of AASC to a glassy sheet of ASG. This requires about 10–20 minutes, preferably 10–15 minutes.

The source of heat may be radiation, conduction or convection means, such as infrared radiation, electric or steam-heated ovens, hot air, or the vapors of an inert organic solvent which boils at 150°–200° C.

If microwave irradiation is used to convert AASC to ASG irradiation is continued to heat the soft anhydrous glassy sheet of AASC at about 150°–200° C., preferably about 160°–180° C., for a period of about 1–2 minutes. The total period under microwave radiation, including the evaporation of water, is about 1½ to 3½ minutes, preferably about 2 to 3 minutes.

The conveyor device leaving an exit port of the tubular heating device, or the microwave oven after converting AASC to ASG, passes to a cooling zone where the soft glassy sheet of ASG is cooled to ambient temperature to form a hard glassy frangible sheet of essentially pure ASG. The ASG is then removed from the conveyor device by suitable means such as scraping, flaking, and the like, and deposited in a receptacle for further processing.

The following examples illustrate embodiments of this invention but it is not limited thereto except as defined in the claims hereafter.

EXAMPLE 1

An aqueous solution containing 60% by weight of ammonium acetylsulfanilylcyanamide and 2% by weight of a dispersant Emcol ® PS 220 (Witco Chemical Corp.) is applied to a moving fiber glass conveyor belt as a 2 mm. thick layer. The conveyor belt is passed through a microwave (2450 MHz.) oven where the microwave irradiation and a stream of hot air removes the water while the temperature of the ammonium acetylsulfanilylcyanamide is allowed to rise to about 70° C. to about 105° C. The residence time in the microwave oven is sufficiently long (75 seconds) so that the glassy sheet leaving the oven is essentially anhydrous. The conveyor belt is then passed into an infrared oven where the temperature of the glassy sheet of dry ammonium acetylsulfanilylcyanamide is raised to 180° C. and maintained at 180° C. for a residence period of 15 minutes to convert the ammonium acetylsulfanilylcyanamide to a glassy sheet of dry acetylsulfaguanidine. The glassy acetylsulfaguanidine leaving the infrared oven is scraped off the belt and is recovered in a hooper. The yield of acetylsulfaguanidine is 96% based on ammonium acetylsulfanilylcyanamide charged.

EXAMPLE 2

The procedure of Example 1 is used except that the essentially anhydrous glassy sheet of ammonium acetylsulfanilylcyanamide is maintained in the microwave oven where the temperature of the sheet is allowed to rise to 160°–180° C. After exposure for a total residence time of 3–4 minutes in the oven the acetylsulfaguanidine is recovered in the manner of Example 1.

EXAMPLE 3

The procedure of Example 1 is used except that the essentially anhydrous sheet of ammonium acetylsulfanilylcyanamide is heated at 180°–200° C. for a period of 15 minutes in an electric oven. At the end of this time the sheet of acetylsulfaguanidine is cooled to 25° C. and crystalline acetylsulfaguanidine is recovered in the manner of Example 1.

I claim:

1. A process for preparing acetylsulfaguanidine which comprises: heating ammonium acetylsulfanilylcyanamide to about 150°–200° C. to form acetylsulfaguanidine; and cooling and recovering the same, the improvement comprising, preliminary to the heating step:

adding a concentrated aqueous solution of ammonium acetylsulfanilylcyanamide as a thin layer to a container;

subjecting said layer to microwave radiation for between about 30–90 seconds to form a soft glassy sheet of essentially anhydrous ammonium acetylsulfanilylcyanamide having a temperature between about 70°–130° C.; and removing said sheet from said microwave radiation.

2. The process according to claim 1 wherein said aqueous solution contains 50–60% by weight by ammonium acetylsulfanilylcyanamide, said layer is subjected to microwave radiation for about 60–80 seconds to form said sheet of anhydrous ammonium acetylsulfanilylcyanamide having a temperature between about 70°–105° C., and said sheet is heated to about 180°–200° C. between about 10–15 minutes to form said glassy sheet of acetylsulfaguanidine.

3. The process according to claim 1 wherein said heating means is infrared radiation.

4. The process according to claim 3 wherein said aqueous solution contains 50–60% by weight of ammonium acetylsulfanilylcyanamide, said layer is subjected to microwave radiation for about 60–80 seconds to form said sheet of anhydrous ammonium acetylsulfanilylcyanamide having a temperature of about 70°–105° C., and in the heating step said sheet is resubjected to microwave radiation at about 160°–180° C. for between about 1–2 minutes to form a glassy sheet of acetylsulfaguanidine.

* * * * *